United States Patent
Vu et al.

(10) Patent No.: US 6,381,303 B1
(45) Date of Patent: *Apr. 30, 2002

(54) X-RAY MICROANALYZER FOR THIN FILMS

(75) Inventors: Long Vu, Round Rock, TX (US); Boris Yokhin, Nazareth Illit (IL); Isaac Mazor, Haifa (IL); Amos Gvirtzman, Moshav Zippori (IL)

(73) Assignee: Jordan Valley Applied Radiation Ltd., Migdal Ha'emek (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/408,894

(22) Filed: Sep. 29, 1999

(51) Int. Cl.[7] .............................................. G01N 23/223
(52) U.S. Cl. ............................................ 378/46; 378/90
(58) Field of Search ............................. 378/44, 45, 46, 378/49, 50, 86, 88, 89, 90

(56) References Cited

U.S. PATENT DOCUMENTS

| | | | |
|---|---|---|---|
| 3,980,568 A | * 9/1976 | Pitchford et al. | 378/49 |
| 4,725,963 A | 2/1988 | Taylor et al. | 364/507 |
| 4,916,720 A | * 4/1990 | Yamamoto et al. | 378/81 |
| 5,003,569 A | 3/1991 | Okada et al. | 378/70 |
| 5,619,548 A | 4/1997 | Koppel | 378/70 |
| 5,740,226 A | 4/1998 | Komiya et al. | 378/70 |
| 5,923,720 A | 7/1999 | Barton et al. | 378/84 |
| 5,937,026 A | * 8/1999 | Satoh | 378/44 |
| 6,108,398 A | 8/2000 | Mazor et al. | 378/45 |

FOREIGN PATENT DOCUMENTS

| | | |
|---|---|---|
| EP | 0 423 803 B1 | 3/1997 |
| JP | 8-136479 | 5/1996 |
| JP | 8-220027 | 8/1996 |
| JP | 10-318737 | 12/1998 |
| JP | 10-325814 | 12/1998 |
| JP | 10-185846 | 9/1999 |

OTHER PUBLICATIONS

Naudon et al., "New Apparatus for Grazing X–ray Reflectometry in the Angle–Resolved Dispersive Mode" Journal of Applied Crystallography 22 (1989) p. 460.

Lengeler "X–ray Reflection, a New Tool for Investigating Layered Structures and Interfaces" Advances in X–ray Analysis 35 (1992), p. 127.

Leenaers et al., "Applications of Glancing Incidence X–ray Analysis" X–ray Spectrometry 26 (1997), p. 115.

Wiener et al., "Characterization of Titanium Nitride Layers by Grazing–Emission X–ray Flourescence Spectrometry", Applied Surface Science 125 (1998), p. 129.

Windover et al., "Thin Film Density Determination by Multiple Radiation Energy Dispersive X–ray Reflectivity", 47th Annual Denver X–ray Conference (Aug., 1998).

Funahashi et al., BST Thin Film Evaluation Using X–ray Flourescence and Reflectivity Method, 47th Annual Denver X–ray Conference (Aug., 1998).

(List continued on next page.)

Primary Examiner—David P. Porta
(74) Attorney, Agent, or Firm—Christie, Parker & Hale, LLP

(57) ABSTRACT

Apparatus for X-ray microanalysis of a sample includes an X-ray source, which irradiates a spot having a dimension less than 500 μm on a surface of the sample. A first X-ray detector captures fluorescent X-rays emitted from the sample, responsive to the irradiation, at a high angle relative to the surface of the sample. A second X-ray detector captures X-rays from the spot at a grazing angle relative to the surface of the sample. Processing circuitry receives respective signals from the first and second X-ray detectors responsive to the X-rays captured thereby, and analyzes the signals in combination to determine a property of a surface layer of the sample within the area of the spot.

26 Claims, 4 Drawing Sheets

OTHER PUBLICATIONS

Remmel et al., "Development of an XRF Metrology Method for Composition and Thickness of Barium Strontium Titanate Thin Films", 47$^{th}$ Annual Denver X-ray Conference (Aug., 1998).

J.T. Radtke and D.W. Beard, "A New Position Sensitive Detector for X-ray Diffractometry", Advances in X-Ray Analysis, vol. 36, J. V. Gilfrich et al Eds; Plenum Press, new York, 1993 (*).

G.M. Zorm, "The New Siemens X-ray Reflectometer. A Tool with Outstanding Capabilities"; Siemens Analytical Application No. 337; Mar. 1994 (*).

"Fast X-ray Reflectometry Tool for Film Thickness Measurement"; AIMA Technical Note R02, 1999. (Month unknown, but before May 1999). (*).

S. Terada, "Introduction to SMAT200 Film Thickness Gauge", Technos Co. Ltd., Mar. 1998(*).

B. Verman, et al., Confocal Graded d-Spacing Multilayer Beam Conditioning Optics, 47$^{th}$ Annual Denver X-ray Conference, Aug. 1998 (*).

A.E. Braun, "Inspection, Measurement & Test", Semiconductor International, Feb. 1998(*).

* cited by examiner

X-RAY MICROANALYZER FOR THIN FILMS

FIELD OF THE INVENTION

The present invention relates generally to analytical instruments, and specifically to instruments and methods for thin film analysis using X-rays.

BACKGROUND OF THE INVENTION

The National Technology Roadmap for Semiconductor (NTRS), published in 1997 by the Semiconductor Industry Association (SIA), indicates that metrology and testing is one of the "Grand Challenges" facing the semiconductor industry as it moves toward advanced technologies, such as 0.18 μm and 0.13 μm design rules. In the area of film thickness metrology, the required accuracy when measuring films with thickness less than 3 nm has stretched the capabilities of current film thickness equipment to its physical limits. In addition, the development of new materials, such as low-k dielectrics to accommodate the need for high speed devices and high-k dielectrics as a replacement for silicon dioxide, also require new capabilities for film thickness metrology.

Traditionally, films processed in semiconductor tabs are classed as transparent or opaque, requiring two distinct classes of film thickness metrology systems: optical equipment for thickness measurement of transparent films, and non-optical equipment for opaque films. Non-optical thickness measurement systems include laser acoustic devices, four-point probes, profilometers and X-ray fluorescent spectroscopy equipment.

Optical equipment, such as reflectometers and ellipsometers, have been widely used in thickness measurement and characterization of dielectric and other transparent films in semiconductor fabs. However, as the gate silicon dioxide thickness is reduced to less than 3 nm, the uncertainty in accuracy of these optical technologies, due to the difference in the assumed optical properties between bulk and thin film structures, is practically too large to be used for monitoring and controlling process equipment. For work with high-k and low-k dielectric films, additional film properties, such as composition and/or mass density, must also be known. These needs are not satisfied by available optical equipment.

Resistivity measurement based on four-point probe techniques has been used to deduced the thickness of metal films or other materials that are highly absorptive to optical radiation. Profilometers are also used to measure a step height at the surface of a sample, and the thickness of the top layer on the sample is deduced from the step height. These measurement technique are destructive, due to the contact between the measurement probes and the films under investigation. Furthermore, they are capable of measuring only the top surface layer, and the accuracy of thickness measurement is highly dependent on the condition of the measurement probes. In addition, the resistivity measurement of the four-point probe is highly susceptible to error when the materials under investigation vary in composition or density.

X-ray fluorescent spectroscopy has also been used to measure the thickness, composition and other properties metal and other films. This technique, however, is incapable of analyzing multilayer film structures that contain the same element in more than one layer, and it is ineffective when the elements to be analyzed are of low atomic number (Z). The high-power X-ray radiation used to excite the sample is destructive, and the measurement process is generally time-consuming and requires extensive calibration in order to obtain quantitative results.

Recently, the emergence of laser acoustic technologies has provided the capability of measuring multi-layer metal film structures. In operation, such techniques require layers of metal or low elastic constant materials in order to launch and sense an acoustic wave, which is used to probe the sample under investigation. The fundamental drawback of laser acoustic measurement is its inability to launch or sense an acoustic wave in dielectric films due to the high elastic constant of such films.

X-ray reflectometry (XRR) is a well-known technique for measuring the thickness, electron density and surface quality of thin film layers deposited on a substrate. Conventional X-ray reflectometers are sold by a number of companies, among them Technos (Osaka, Japan), Siemens (Munich, Germany) and Bede Scientific Instrument (Durham, UK). Such reflectometers typically operate by irradiating a sample with a beam of X-rays at grazing incidence, i.e., at a small angle relative to the surface of the sample, near the total external reflection angle of the sample material. Sequential measurement of X-ray intensity reflected from the sample as a function of angle gives a pattern of interference fringes, which is analyzed to determine the properties of the film layers responsible for creating the fringe pattern. The effectiveness of XRR is limited to layers that are less than 200 nm thick and have a surface roughness of no more than about 10 nm.

A method for performing the required analysis to determine film thickness from XRR data is described, for example, in U.S. Pat. No. 5,740,226, to Komiya et al., whose disclosure is incorporated herein by reference. Komiya et al. describe the application of their method to various types of thin films that are used in semiconductor electronic devices, including specifically $SiO_2$, Ti and TiN.

U.S. Pat. No. 5,619,548, to Koppel, whose disclosure is likewise incorporated herein by reference, describes an X-ray thickness gauge based on reflectometric measurement. A curved, reflective X-ray monochromator is used to focus X-rays onto the surface of a sample. A position-sensitive detector, such as a photodiode detector array, senses the X-rays reflected from the surface and produces an intensity signal as a function of reflection angle. The angle-dependent signal is analyzed to determine properties of the structure of a thin film layer on the sample, including thickness, electron density and surface roughness. In order to determine the mass density of the layers, however, prior information is required regarding the composition of the analyzed layer, which cannot be determined based on XRR alone.

U.S. Pat. No. 5,923,720, to Barton et al., whose disclosure is incorporated herein by reference, also describes an X-ray spectrometer based on a curved crystal monochromator. The monochromator has the shape of a tapered logarithmic spiral, which is described as achieving a finer focal spot on a sample surface than prior art monochromators. Barton et al. calculate that the theoretical minimum spot size achievable by their monochromator is 5 nm. X-rays reflected or diffracted from the sample surface are received by a position-sensitive detector. It is suggested that the X-ray spectrometer may be used in surface mapping and film thickness measurements, with application to real-time in situ control of a film deposition system, such as systems used in MOCVD.

U.S. Pat. No. 5,003,569 to Okada et al., whose disclosure is incorporated herein by reference, describes a thickness determination method for organic films based on X-ray reflectometry. The organic film to be measured is irradiated with X-rays at a certain angle of incidence, and the angle is varied in order to find the angle of reflection at which the X-ray intensity reaches a peak. The peak is used to find the thickness of the film.

Another common method of X-ray reflectometric measurement is described, for example, in an article by Naudon et al., entitled "New Apparatus for Grazing X-ray Reflectometry in the Angle-Resolved Dispersive Mode," in *Journal of Applied Crystallography* 22 (1989), p. 460, which is incorporated herein by reference. A divergent beam of X-rays is directed toward the surface of a sample at grazing incidence, and a detector opposite the X-ray beam source collects reflected X-rays. A knife edge is placed close to the sample surface immediately above a measurement location in order to cut off the primary X-ray beam, so that only X-rays reflected from the measurement location reach the detector. A monochromator between the sample and the detector (rather than between the source and sample, as in U.S. Pat. No. 5,619,548) selects the wavelength of the reflected X-ray beam that is to reach the detector. The reflected X-ray signal is used, inter alia, to calculate the density of a surface layer of the sample, although in this method, too, a priori knowledge of the composition of the sample is required in order to find the mass density.

An article by Lengeler, entitled "X-ray Reflection, a New Tool for Investigating Layered Structures and Interfaces," in *Advances in X-ray Analysis* 35 (1992), p. 127, which is incorporated herein by reference, describes a system for measurement of grazing-incidence X-ray reflection, in which X-ray fluorescence is also measured. A sample is irradiated by an X-ray source at grazing incidence. One X-ray detector captures X-rays reflected (likewise at grazing incidence) from the surface of the sample, while another detector above the sample captures X-ray fluorescence emitted by the sample due to excitation by the X-ray source. Analysis of the fluorescence emitted when the sample is excited at an angle below the critical angle for total external reflection of the incident X-rays, as described in this article, is known in the art as total reflection X-ray fluorescence (TXRF) analysis.

Another article, by Leenaers et al., entitled "Applications of Glancing Incidence X-ray Analysis," in *X-ray Spectrometry* 26 (1997), p. 115, which is incorporated herein by reference, describes a method known as glancing incidence X-ray analysis (GIXA). The method combines X-ray reflectivity and angle-dependent X-ray fluorescence measurements to obtain a structural and chemical analysis of a sample.

An article by Wiener et al., entitled "Characterization of Titanium Nitride Layers by Grazing-Emission X-ray Fluorescence Spectrometry," in *Applied Surface Science* 125 (1998), p. 129, which is incorporated herein by reference describes an alternative method for analyzing thin film layers. A sample is irradiated by an X-ray source at normal or near-normal incidence, and fluorescent X-ray photons emitted by the sample are collected at a grazing angle, close to the surface. The spectrum of the collected photons is analyzed by a technique of wavelength dispersion, as is known in the art, and the distribution of photons by emission angle is determined, as well. The resultant data provide information about the thickness and composition of thin film layers on the sample.

Energy dispersion techniques can also be used to analyze the spectral distribution of reflected photons, as described, for example, in a paper by Windover et al., entitled "Thin Film Density Determination by Multiple Radiation Energy Dispersive X-ray Reflectivity," presented at the 47th Annual Denver X-ray Conference (August, 1998), which is incorporated herein by reference.

Another paper presented at the August, 1998, Denver X-ray Conference, by Funahashi et al., entitled "BST Thin Film Evaluation Using X-ray Fluorescence and Reflectivity Method," which is incorporated herein by reference, describes further methods that combine XRR and XRF measurements. The paper points out that measuring reflectivity provides structural information, such as thickness and density of thin films, which can be useful in preparing accurate calibration constants for inline XRF measurements. Moreover, the refractive indices of the thin film, which are needed for accurately fitting the interference pattern of the reflected signal to an optical model so as to find the film layer thickness, can be calculated based on the composition of the film material as determined by XRF. A paper by Remmel et al., entitled "Development of an XRF Metrology Method for Composition and Thickness of Barium Strontium Titanate Thin Films," also presented at the August, 1998, Denver X-ray Conference and incorporated herein by reference, describes methods similar to those of Funahashi et al., in which XRF is combined with film thickness measurements based on spectroscopic ellipsometry and X-ray reflectivity.

SUMMARY OF THE INVENTION

It is an object of the present invention to provide improved methods and apparatus for analysis of the properties of surface layers of a sample.

It is a further object of some aspects of the present invention to provide improved methods and apparatus for thin film evaluation, particularly for use in the production of integrated circuits on semiconductor wafers.

It is yet a further object of some aspects of the present invention to provide methods and apparatus for X-ray microanalysis of features at the surface of a sample.

In preferred embodiments of the present invention, an X-ray microanalyzer comprises at least one X-ray source and at least two X-ray detector devices. Most preferably, the detector devices comprise detector arrays. The X-ray source emits X-rays, which are focused to a fine spot on the surface of a sample under analysis, causing emission of fluorescent X-rays photons from the spot. Typically the sample comprises a semiconductor wafer on which one or more thin film layers have been deposited in a predetermined pattern. Preferably, the X-rays are focused by a monolithic capillary array, most preferably as described in U.S. patent application Ser. No. 09/114,789, which is assigned to the assignee of the present patent application and incorporated herein by reference. The capillary array focuses the X-rays to a spot that is less than 500 $\mu$m in diameter, more preferably less than 100 $\mu$m in diameter, and most preferably approximately 50 $\mu$m in diameter, so that the focused X-ray irradiation can be substantially confined to the area of a selected feature on the wafer, such as a scribe line or an element of an integrated circuit.

The detector arrays comprise a first array, which is positioned opposite the sample to capture X-ray fluorescence emitted therefrom at relatively high angles to the surface, and a second array, which is positioned so as to capture X-rays at a relatively low angle, preferably a grazing angle with respect to the surface. The high-angle fluorescent X-rays captured by the first array are analyzed, primarily for the purpose of determining the elemental composition and/or thickness of the sample within the feature on which the X-ray spot is focused. The low-angle X-rays captured by the second array are analyzed for the purpose of determining the thickness and density and roughness of one or more thin film layers at the surface of the sample. The results of the analysis of the X-rays captured by the two arrays are combined to derive a complete, calibrated analysis of the selected feature, preferably including the composition, thickness and density of one or more thin film layers within the feature.

Thus, while X-ray analyzers known in the art can give only a gross picture, averaged over relatively large areas of a wafer or other sample, microanalyzers in accordance with preferred embodiments of the present invention are capable of analyzing surface layer properties in a small, precisely-selected spot. The present invention is thus particularly useful in non-destructive analysis of the properties of elements of integrated circuits on a semiconductor wafer, both in various stages of production and in post-production testing. It enables the mass density of thin film layers to be measured directly, in a single measurement operation, without a priori knowledge of the film composition.

In some preferred embodiments of the present invention, the X-ray photons captured by the second detector array are fluorescent photons emitted by the sample at low angles, so that only a single X-ray source provides excitation for both high-angle and grazing-angle emission measurements. In other preferred embodiments, however, a second X-ray source is positioned so as to irradiate the sample at grazing incidence, and the second detector array is used to capture X-rays reflected from the sample surface. The use of reflectometry, rather than low-angle fluorescence measurement, provides a higher signal flux and therefore faster measurement throughput. The beam of the second X-ray source is preferably monochromatized either before or after impinging on the sample, as is known in the art. Most preferably, the beam is focused to a fine spot describing a generally oblong shape on the sample, wherein the spot has a transverse dimension on the order of the focused spot size created by the X-ray source used for fluorescence excitation.

There is therefore provided, in accordance with a preferred embodiment of the present invention, apparatus for X-ray microanalysis of a sample, including:

an X-ray source, which irradiates a spot having a dimension less than 500 $\mu$m on a surface of the sample;

a first X-ray detector, which captures fluorescent X-rays emitted from the sample, responsive to the irradiation, at a high angle relative to the surface of the sample;

a second X-ray detector, which captures X-rays from the spot at a grazing angle relative to the surface of the sample; and processing circuitry, which receives respective signals from the first and second X-ray detectors responsive to the X-rays captured thereby, and which analyzes the signals in combination to determine a property of a surface layer of the sample within the area of the spot.

Preferably, the spot has a dimension less than 100 m. Most preferably, the spot has a dimension of about 50 $\mu$m or less.

Preferably, the first and second X-ray detectors include detector arrays, wherein the first detector array includes a plurality of detector elements disposed around a beam axis of the X-ray source. Preferably, the second detector captures fluorescent X-rays emitted from the sample at the grazing angle.

In a preferred embodiment, the first detector array captures fluorescent X-rays emitted from the sample when the X-ray source irradiates the sample at an angle below a total external reflection angle of the sample.

Preferably, the X-ray source includes a first X-ray source, which irradiates the spot along an axis generally perpendicular to the surface of the sample, and including a second X-ray source, which irradiates an area of the surface including the spot at the grazing angle, so that the second X-ray detector captures reflected X-rays from the second source. Most preferably, the area irradiated by the second X-ray source has a transverse dimension approximately equal to the dimension of the spot irradiated by the first X-ray source. Preferably, the apparatus includes a monochromator, which monochromatizes X-rays from the second X-ray source.

There is further provided, in accordance with a preferred embodiment of the present invention, apparatus for X-ray microanalysis of integrated circuits produced on a semiconductor wafer, including:

an X-ray source, which irradiates an area on a surface of the wafer corresponding to a selected feature of the integrated circuits;

a first X-ray detector, which captures fluorescent X-rays emitted from the irradiated area, responsive to the irradiation, at a high angle relative to the surface of the wafer;

a second X-ray detector, which captures X-rays from the irradiated area at a grazing angle relative to the surface of the wafer; and processing circuitry, which receives respective signals from the first and second X-ray detectors responsive to the X-rays captured thereby, and which analyzes the signals in combination to determine a property of the selected feature of the integrated circuits.

Preferably, the integrated circuits are produced by depositing a thin film layer on the wafer, and wherein the property of the selected feature includes a thin film property, most preferably including a composition of the film, a thickness of the film and/or a density of the film. In a preferred embodiment, multiple thin film layers are deposited on the wafer, and wherein the processing circuitry determines properties of two or more of the multiple layers.

There is also provided, in accordance with a preferred embodiment of the present invention, a method for X-ray microanalysis of a sample, including:

irradiating a spot having a dimension less than 500 $\mu$m on a surface of the sample;

capturing fluorescent X-rays emitted from the sample, responsive to the irradiation, at a high angle relative to the surface of the sample;

capturing grazing angle X-rays from the spot at a grazing angle relative to the surface of the sample; and receiving respective signals from the first and second X-ray detectors responsive to the X-rays captured thereby; and analyzing the signals in combination to determine a property of a surface layer of the sample within the area of the spot.

Preferably, the sample includes a semiconductor wafer, and irradiating the spot includes selectively irradiating a particular feature of integrated circuits produced on the wafer, wherein analyzing the signals includes determining a property of a thin film on the wafer used in producing the integrated circuits.

In preferred embodiments, multiple thin film layers are deposited on the wafer, and determining the property of the thin film includes determining properties of two or more of the multiple layers. In one such preferred embodiment, the multiple layers include a copper layer, a tantalum layer and a tantalum nitride layer, wherein the multiple layers include an intermediate layer dielectric. In another preferred embodiment, the thin film has a thickness substantially greater than 200 nm.

The present invention will be more fully understood from the following detailed description of the preferred embodiments thereof, taken together with the drawings in which:

DETAILED DESCRIPTION OF PREFERRED EMBODIMENTS

Figure 1A:
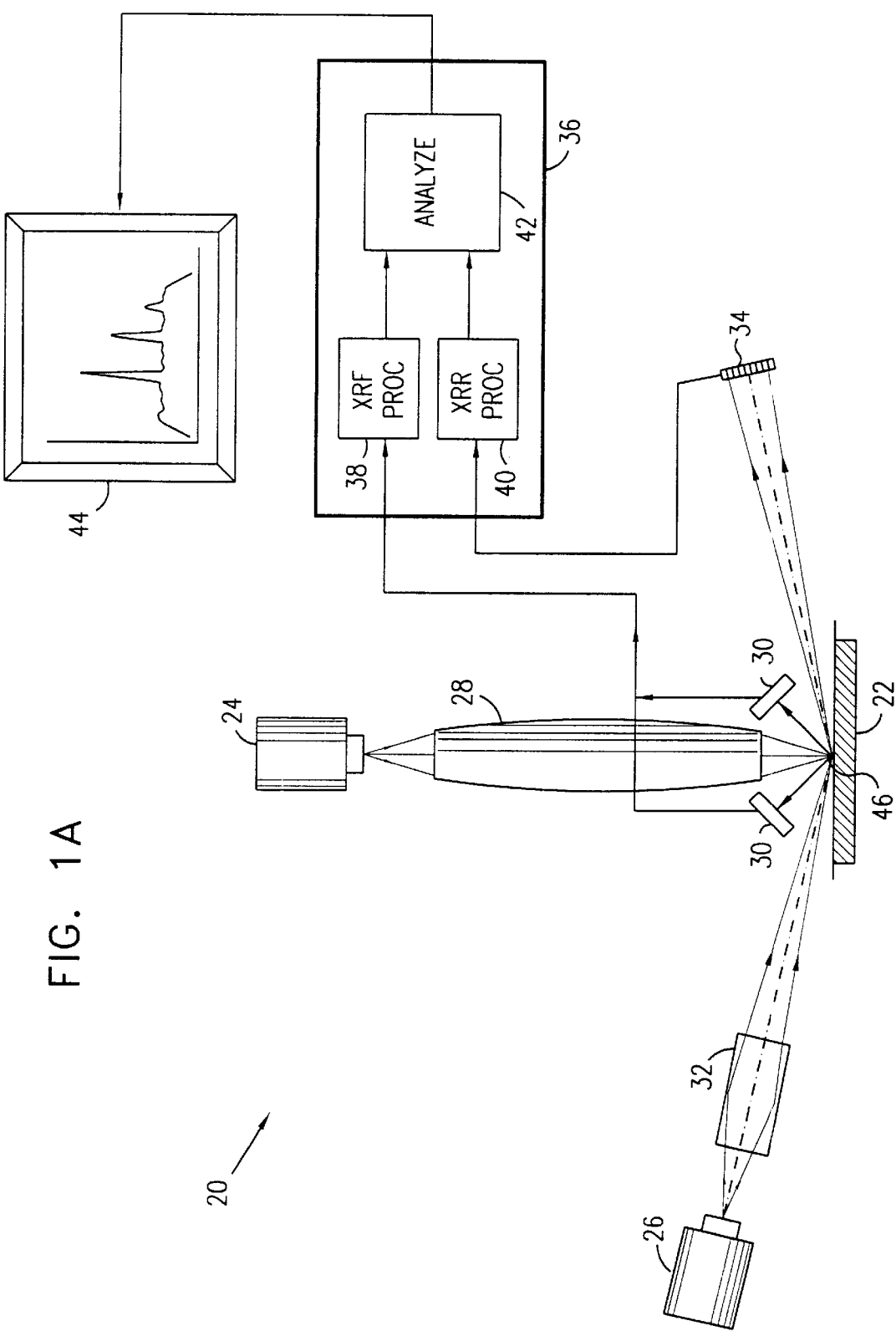
FIG. 1A is a schematic illustration of a system for X-ray microanalysis, in accordance with a preferred embodiment of the present invention.

FIG. 1A is a schematic illustration of a system 20 for X-ray microanalysis of a sample 22, in accordance with a preferred embodiment of the present invention. A first X-ray source 24, typically an X-ray tube, irradiates sample 22 through focusing optics 28, which preferably comprise a monolithic polycapillary array. Alternatively, optics 28 may comprise a monocapillary optic and/or X-ray collimating pinholes, or any other suitable means known in the art. The X-ray tube, polycapillary array and other X-ray detection and signal processing components used for X-ray fluorescence (XRF) detection in system 20 are described in greater detail in the above-mentioned U.S. patent application Ser. No. 09/114,789. Optics 28 collect the X-rays from source 24 and focus them to a spot 46 on the sample. Most preferably, spot 26 is substantially circular with a diameter of the order of 50 µm.

Fluorescent X-rays, emitted by sample 22 in response to the irradiating X-rays, are collected by a plurality of detectors 30, preferably PIN diodes arranged in a circular array, as described in the above-mentioned U.S. patent application. Although for the sake of simplicity of illustration, only two detectors 30 are shown in FIG. 1A, any suitable number of detectors may be used. Most preferably, an array of four or more such detectors is used, with the detectors angled towards spot 46 as shown in FIG. 1A, in order to increase the active area presented to the spot. Signals from detectors 30 are transferred to a XRF processing channel 38 of a processing unit 36, which determines a spectrum of the captured X-rays, preferably using methods of energy-dispersive XRF processing (ED-XRF) known in the art.

Optionally, a second X-ray source 26, preferably an X-ray tube, irradiates spot 46 on sample 22 at a grazing angle, in order to generate X-ray reflectance (XRR) signals at a second detector array 34. Preferably, radiation emitted by source 26 is filtered and focused onto the area of spot 46 by a monochromator 32, which is described in greater detail hereinbelow. Further preferably, array 34 comprises a row of PIN diode detectors with integrated parallel processing circuitry, as described in a U.S. patent application, filed on even date, entitled "X-ray Array Detector," which is assigned to the assignee of the present patent application and whose disclosure is incorporated herein by reference. Alternatively, array 34 comprises a commercially-available reflectance measurement device or any suitable type of CCD, photodiode or gas detector, as are known in the art. The XRR signals are processed by an XRR processing channel 40 in order to determine a distribution of reflected X-ray intensity as a function of angle.

Figure 1B:
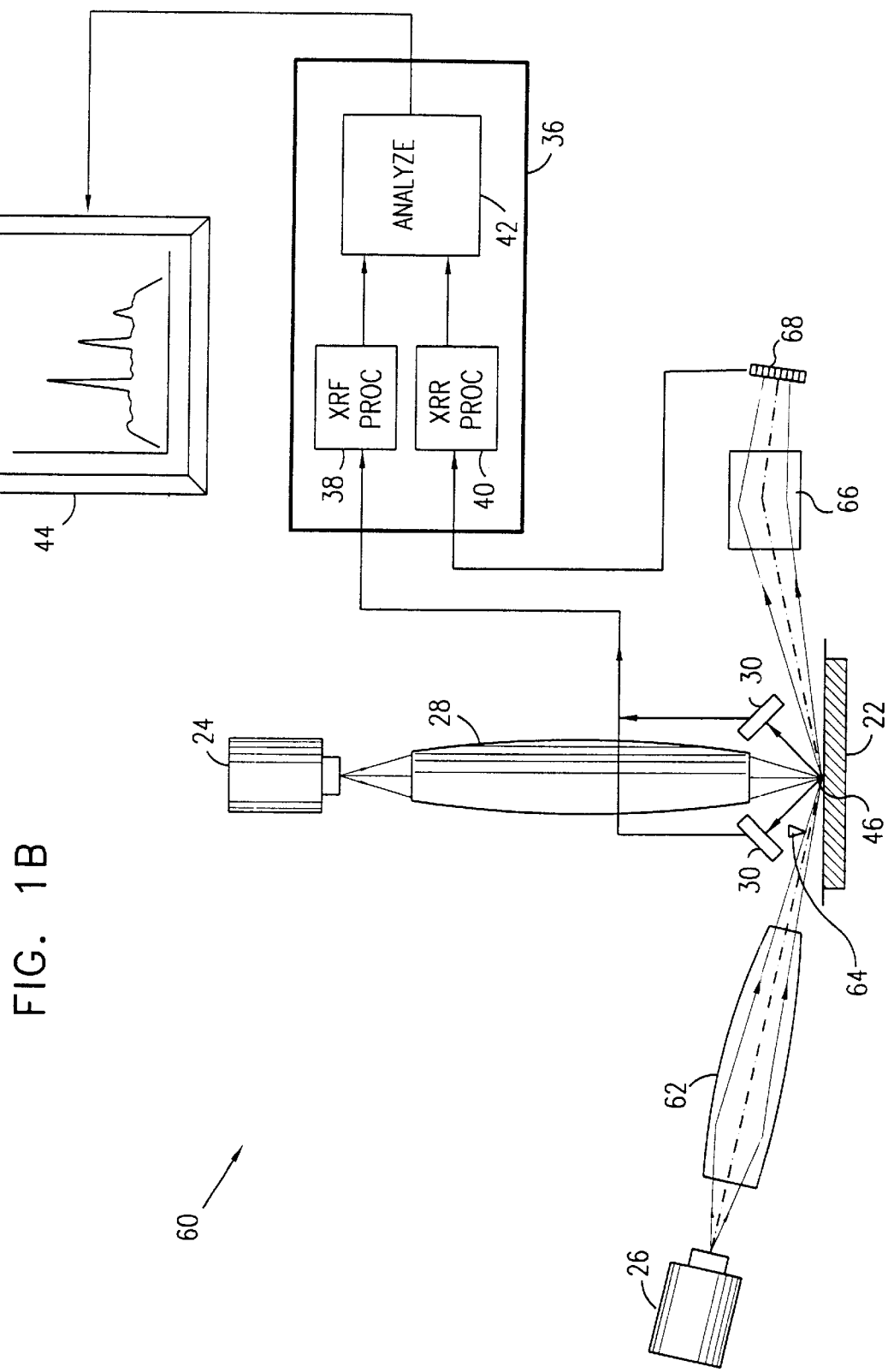
FIG. 1B is a schematic illustration of a system for X-ray microanalysis, in accordance with an alternative embodiment of the present invention.

FIG. 1B is a schematic illustration of a system 60 for X-ray microanalysis of sample 22, in accordance with an alternative embodiment of the present invention. In this case, radiation from source 26 is focused onto sample 22 by focusing optics 62, preferably comprising a polycapillary array like array 28. A monochromator 66 is positioned between sample 22 and a detector 68, rather than or in addition to monochromator 32 in the position shown in FIG. 1A. A knife edge 64 is placed in proximity to the surface of the sample in order to prevent primary X-rays from source 26 from reaching detector 68, in a configuration similar to that described, for example, in the above-mentioned article by Naudon et al. Unlike systems known in the art, knife edge 64 in system 60 is displaced relative to spot 46, typically by about 2 cm toward source 26, in order not to interfere with X-rays emitted from the sample toward detectors 30. Preferably, detector 68 comprises a detector array or other position-sensitive detector, as described hereinabove. Alternatively, the detector, monochromator or source 26 is scanned mechanically to provide angle-dependent reflectance data.

In still a further preferred embodiment, X-ray source 26 is not used, and instead array 34 (or detector 68) captures fluorescent X-rays emitted from spot 46 at grazing angles, as described, for example, in the above-mentioned article by Wiener et al. Signals generated by array 34 are processed to determine the intensity distribution of the captured X-rays as a function of angle and, preferably, of X-ray energy. This processing is carried out by processing circuitry integrated with array 34 and/or by XRR processing channel 40 (which in this case does not process X-ray reflectivity signals, but rather grazing angle X-ray emission).

In yet another possible embodiment, source 24 is not used, and X-ray excitation in the area of spot 46 is provided by source 26. In this embodiment, system 20 or system 60 can be used for glancing incidence X-ray analysis, as described in the above-mentioned article by Leenaers et al.

A signal analyzer 42 receives the spectral data generated by XRF processing channel 38 and the angular intensity distribution data generated by XRR processing channel 40. The spectral and angular data are jointly analyzed, as described further hereinbelow, to generate information regarding the composition, thickness, density and other properties of a surface layer or layers of sample 22 at spot 46. Typically sample 22 comprises a semiconductor wafer, and the analysis relates to thin film layers used in producing an integrated circuit element on the wafer. At the level of resolution achieved by system 20 or 60, it is possible to focus spot 46 on a particular circuit feature and obtain specific data regarding the thin film layers within the feature. Alternatively or additionally, the spot may be focused on a scribe line on the wafer, so as to analyze special long, narrow test structures that are typically produced in this region of production wafers. The results are presented on a display 44 or are otherwise printed out or stored, as is known in the art.

Figure 2:
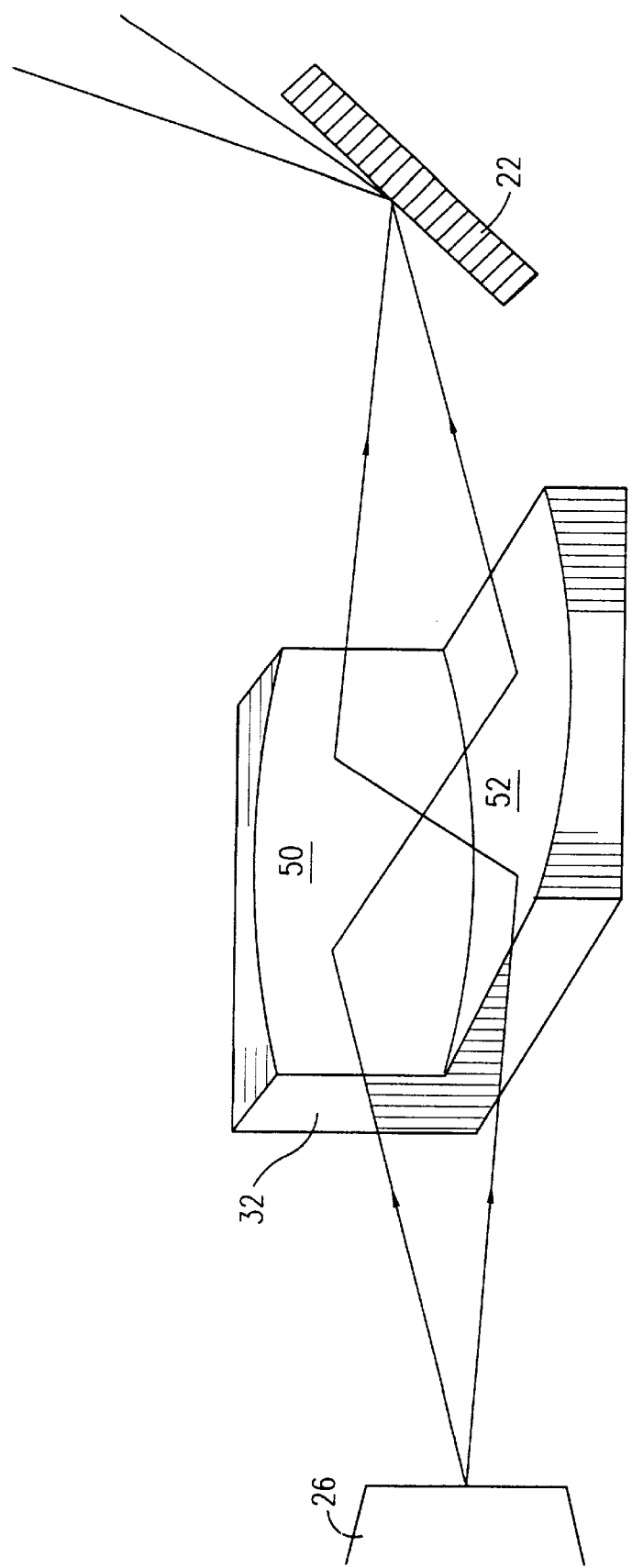
FIG. 2 is a schematic, pictorial representation of a monochromator used in the system of FIG. 1A, in accordance with a preferred embodiment of the present invention.

FIG. 2 is a schematic, pictorial illustration showing details of monochromator 32, in accordance with a preferred embodiment of the present invention. The monochromator preferably comprises two curved surfaces 50 and 52 in a configuration known as a side-by-side Kirkpatrick-Baez optical scheme. Monochromators of this sort, with a multi-layer coatings on surfaces 50 and 52, are available from Osmic Inc., of Troy, Mich. Alternatively, monochromator 32 may comprise a X-ray Doubly-bent Focusing Crystal Optic, preferably made of mica crystal with a focal spot size of 52×78 µm, manufactured by XOS (X-ray Optical Systems), Inc., of Albany, N.Y.

Figure 3:
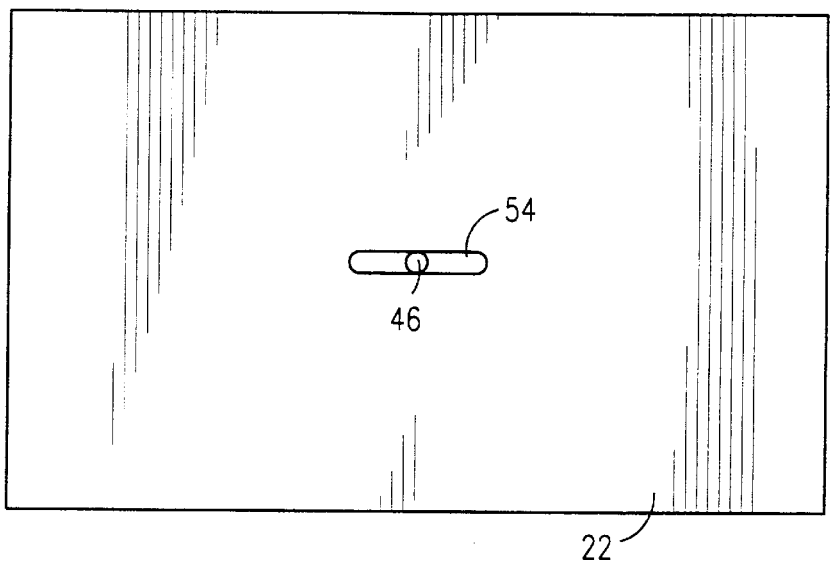
FIG. 3 is a schematic top view of a sample irradiated by X-rays in the system of FIG. 1A or 1B, in accordance with a preferred embodiment of the present invention.

FIG. 3 is a schematic top view of sample 22, illustrating focal spot 46 of the beam from source 24, focused on the sample by optics 28, in accordance with a preferred embodiment of the present invention. When source 26 is not used, and array 34 (or detector 68) collects only grazing-angle fluorescent radiation due to irradiation by source 24, substantially all of the collected radiation originates from spot 46. This configuration allows the composition, thickness, density and other measurements to be made with a resolution equal to the focal spot size, i.e., about 50 µm in the present example.

Alternatively, when source 26 is used, monochromator 32 focuses the beam onto an oblong focal area 54, having a long dimension parallel to the X-ray beam axis. The spot dimensions achieved using focusing monochromator 32 are typically about 40 µm wide by 2 mm long. Although it is not generally possible to confine the long dimension of focal area 54 within the bounds of spot 46, the focus of the monochromator is fine enough so that the transverse dimension of the area is no wider than the spot diameter, as shown in FIG. 3. The use of source 26 then enables thickness and density measurements to be made on surface layers of sample 22 with enhanced throughput, while the high resolution of spot 46 is maintained at least in the transverse direction.

Figure 4:
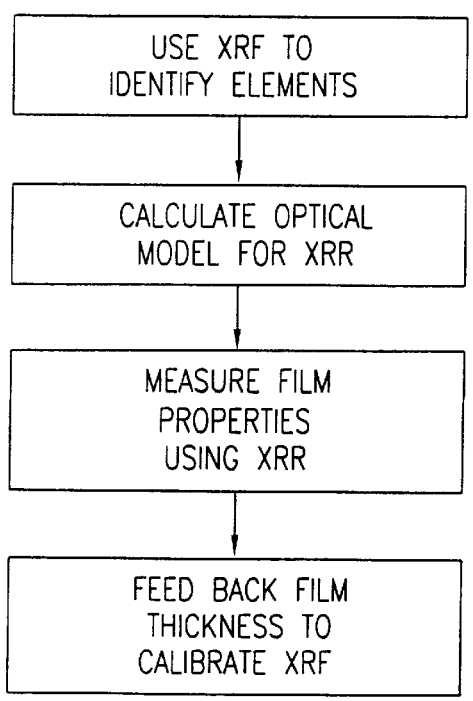
FIG. 4 is a flow chart that schematically illustrates a method for determining properties of a thin film using the system of FIG. 1A or 1B, in accordance with a preferred embodiment of the present invention.

FIG. 4 is a flow chart that schematically illustrates a method using system 20 or 60 for analyzing properties of sample 22 at spot 46, in accordance with a preferred embodiment of the present invention. XRF and XRR data collected by the system are used interdependently to determine the thickness and composition of surface layers of the sample. A priori knowledge of the composition of the layers is not requires, and typically the determination is made in fewer computational steps and with greater precision than using XRF or XRR alone.

XRF data collected from detectors 30 are processed and analyzed to make a qualitative determination of the elemental composition of the sample. The composition is used to derive a model for use in the grazing angle measurements. Typically, the model includes estimated refractive indices of the surface layer or layers of sample 22 at spot 46, which is function of the density and composition of the layers. Grazing-angle radiation received by detector array 34 is processed to generate an oscillating fringe pattern, due to interference of radiation reflected from the surface layers of sample 22. The pattern typically appears whether the radiation received by the detector is due to reflection of X-rays from source 26 or to fluorescence excited by source 24. The optical model is used to parametrically fit a theoretical interference pattern to the actual measured pattern. Preferably, the Levenberg/Marquatz fitting method is used for this purpose, as is known in the art, but substantially any other suitable numerical fitting method, such as least-squares fitting, may similarly be used. Based on the fit, the thickness and density of the thin film or other upper surface layer or layers are determined, as is known in the art. Optionally, the roughness of the interface between the layers is also determined. In semiconductor processing, using processes such as chemical vapor deposition (CVD), physical vapor deposition (PVD) and/or electro-plating, for example, these parameters may vary from wafer to wafer.

The thickness and density of the surface layers, as determined from the grazing-angle measurements, are then applied to calibrate the XRF data, preferably in real time, while the measurements are being made. Based on the calibration, quantitative elemental concentrations in the sample are derived from the earlier qualitative results. System 20 or 60 thus allows the structure, composition and mass density of the surface layers of the sample to be determined in a single measurement operation, without the use of cumbersome external calibration standards. Alternatively or additionally, differences between calibration standards and the sample under investigation can be determined and taken into account at measurement time. In either case, the determination of the surface layer properties of the sample is made with sufficiently high resolution so that microscopic features of the sample, such as elements of an integrated circuit, can be individually analyzed.

Preferred embodiments of the present invention may be applied to a wide range of integrated circuit wafer metrology applications, for example:

Analysis of Cu/Ta/TaN layers on a silicon substrate. XRR generates a complex spectrum, including weak reflectance signals from inner layers. When XRR is used by itself, nine independent parameters (density, thickness and roughness of each layer) must be adjusted and fitted to the spectrum. As much as an hour of operator-interactive processing may be required for a single measurement. On the other hand, in a preferred embodiment of the present invention, assuming the densities of the copper and tantalum layers are known (since they are pure metal), XRF data are used to find the thickness of the copper layer and the combined thickness of the two tantalum-containing layers. The number of independent parameters that must be fitted to the XRR data is thus reduced to five.

Analysis of Cu/Ta/TaN with intermediate level dielectric (ILD) on top of a Cu lower layer. XRR measurement alone cannot generally reach the lower copper layer. In a preferred embodiment of the present invention, XRF is used to determine the total copper content of the sample. The XRR data are used to determine the thickness, and hence the copper content, of the upper copper layer. This figure is subtracted from the total copper content to determine the thickness of the lower copper layer.

In a similar manner, the combination of XRF and XRR measurements afforded by system 20 or 60 can be used to determine accurately the thickness of multiple film layers that cannot be measured accurately or conveniently using XRR alone or other thickness measurement techniques known in the art. Typical applications include:

Individual layer thickness in TaN/Cu/ILD, seed copper/ TaN/Ta/ILD, seed copper/TaN/TiN/ILD and TiN/Ti/ AlCu.

Thickness measurements over 200 nm of layers of materials such as WN, TaN and TiN.

Detection of trace elements in the surface layer. The position of source 26 in system 20 or 60 may be adjusted so that X-rays therefrom strike the surface of sample 22 below the total external reflection angle. Detectors 30 will then receive TXRF signals, useful in isolating trace elements on or near the sample surface.

Although in preferred embodiments described hereinabove, XRF is used in conjunction with XRR for determination of sample layer thicknesses, it will be appreciated that other thickness measurement techniques, such as ellipsometry, may also be used for this purpose. It will be appreciated that the preferred embodiments described above are cited by way of example, and the full scope of the invention is limited only by the claims.

What is claimed is:

1. Apparatus for X-ray microanalysis of a sample, comprising:

a first X-ray source, which irradiates a spot having a dimension less than 500 µm on a surface of the sample along an axis generally perpendicular to the surface;

a second X-ray source, which irradiates an area of the surface including the spot at a grazing angle relative to the surface;

a first X-ray detector, which captures fluorescent X-rays emitted from the sample, responsive to irradiation by the first X-ray source, at a high angle relative to the surface of the sample;

a second X-ray detector, which captures X-rays from the second X-ray source, which are reflected from the spot at the grazing angle; and processing circuitry, which receives respective signals from the first and second X-ray detectors responsive to the X-rays captured thereby, and which analyzes the signals in combination to determine a property of a surface layer of the sample within the area of the spot.

2. Apparatus according to claim 1, wherein the spot has a dimension less than 100 µm.

3. Apparatus according to claim 2, wherein the spot has a dimension of about 50 µm or less.

4. Apparatus according to claim 1, wherein the first and second X-ray detectors comprise detector arrays.

5. Apparatus according to claim 4, wherein the first detector array comprises a plurality of detector elements disposed around a beam axis of the X-ray source.

6. Apparatus according to claim 1, wherein the second detector captures fluorescent X-rays emitted from the sample at the grazing angle.

7. Apparatus according to claim 1, wherein the sample comprises a semiconductor wafer, and wherein the apparatus is configured so that the irradiated spot falls generally within the area of a selected feature of integrated circuits produced on the wafer.

8. Apparatus according to claim 1, and comprising a monochromator, which monochromatizes X-rays from the second X-ray source.

9. Apparatus according to claim 1, wherein the area irradiated by the second X-ray source has a transverse dimension approximately equal to the dimension of the spot irradiated by the first X-ray source.

10. Apparatus for X-ray microanalysis of integrated circuits produced on a semiconductor wafer, comprising:

a first X-ray source, which irradiates an area on a surface of the wafer corresponding to a selected feature of the integrated circuits along an axis generally perpendicular to the surface;

a second X-ray source, which irradiates an area of the surface including the spot at a grazing angle relative to the surface;

a first X-ray detector, which captures fluorescent X-rays emitted from the irradiated area, responsive to irradiation by the first X-ray source, at a high angle relative to the surface of the wafer;

a second X-ray detector, which captures X-rays from the second X-ray source, which are reflected from the spot at the grazing angle; and processing circuitry, which receives respective signals from the first and second X-ray detectors responsive to the X-rays captured thereby, and which analyzes the signals in combination to determine a property of the selected feature of the integrated circuits.

11. Apparatus according to claim 10, wherein the integrated circuits are produced by depositing a thin film layer on the wafer, and wherein the property of the selected feature comprises a thin film property.

12. Apparatus according to claim 11, wherein the thin film property comprises a composition of the film.

13. Apparatus according to claim 11, wherein the thin film property comprises a thickness of the film.

14. Apparatus according to claim 11, wherein the thin film property comprises a density of the film.

15. Apparatus according to claim 3, wherein multiple thin film layers are deposited on the wafer, and wherein the processing circuitry determines properties of two or more of the multiple layers.

16. A method for X-ray microanalysis of a sample, comprising:

irradiating a spot having a dimension less than 500 µm on a surface of the sample along an irradiation axis generally perpendicular to the surface using a first X-ray source;

irradiating an area of the surface including the spot at a grazing angle relative to the surface, using a second X-ray source;

capturing fluorescent X-rays emitted from the sample, responsive to irradiation of the spot by the first X-ray source, at a high angle relative to the surface of the sample;

capturing X-rays from the second X-ray source reflected from the spot at the grazing angle; and receiving respective first and second signals responsive to the captured fluorescent and reflected X-rays; and analyzing the first and second signals in combination to determine a property of a surface layer of the sample within the area of the spot.

17. A method according to claim 16, wherein irradiating the spot comprises irradiating an area having a dimension less than 100 µm.

18. A method according to claim 17, wherein irradiating the area comprises irradiating an area having a dimension of about 50 µm or less.

19. A method according to claim 16, wherein capturing the grazing angle X-rays comprises capturing fluorescent X-rays emitted from the sample at the grazing angle.

20. A method according to claim 16, wherein irradiating the area of the surface at the grazing angle comprises irradiating an area having a transverse dimension approximately equal to the dimension of the spot that is irradiated along the generally perpendicular axis.

21. A method according to claim 16, wherein the sample comprises a semiconductor wafer, and wherein irradiating the spot comprises selectively irradiating a particular feature of integrated circuits produced on the wafer.

22. A method according to claim 21, wherein analyzing the signals comprises determining a property of a thin film on the wafer used in producing the integrated circuits.

23. A method according to claim 22, wherein multiple thin film layers are deposited on the wafer, and wherein determining the property of the thin film comprises determining properties of two or more of the multiple layers.

24. A method according to claim 23, wherein in the multiple layers comprise a copper layer, a tantalum layer and a tantalum nitride layer.

25. A method according to claim 24, wherein the multiple layers comprise an intermediate layer dielectric.

26. A method according to claim 22, wherein the thin film has a thickness substantially greater than 200 nm.

* * * * *